United States Patent
Borate et al.

(10) Patent No.: US 8,129,369 B2
(45) Date of Patent: Mar. 6, 2012

(54) ANTIFUNGAL COMPOUNDS CONTAINING BENZOTHIAZINONE, BENZOXAZINONE OR BENZOXAZOLINONE AND PROCESS THEREOF

(75) Inventors: Hanumant Bapurao Borate, Pune (IN); Suleman Riyasaheb Maujan, Pune (IN); Sangmeshwer Prabhakar Sawargave, Pune (IN); Ramesh Ganesh Kelkar, Pune (IN); Radhika Dilip Wakharkar, Pune (IN); Mohan Anand Chandavarkar, Mumbai (IN); Sharangi Ravinda Vaiude, Mumbai (IN); Vinay Anant Joshi, Mumbai (IN)

(73) Assignees: Council of Scientific & Industrial Research;, New Delhi, IN (US); FDC Ltd., Maharashtra, IN (US)

( * ) Notice: Subject to any disclaimer, the term of this patent is extended or adjusted under 35 U.S.C. 154(b) by 0 days.

(21) Appl. No.: 13/121,730

(22) PCT Filed: Oct. 16, 2009

(86) PCT No.: PCT/IN2009/000594
§ 371 (c)(1),
(2), (4) Date: Mar. 30, 2011

(87) PCT Pub. No.: WO2010/046931
PCT Pub. Date: Apr. 29, 2010

(65) Prior Publication Data
US 2011/0183968 A1 Jul. 28, 2011

(30) Foreign Application Priority Data
Oct. 24, 2008 (IN) .......................... 2306/MUM/2008

(51) Int. Cl.
C07D 413/06 (2006.01)
C07D 417/06 (2006.01)
A61K 31/423 (2006.01)
A61K 31/536 (2006.01)

(52) U.S. Cl. .................. 514/224.2; 514/230.5; 514/376; 544/52; 544/105; 548/219

(58) Field of Classification Search .................... 544/52, 544/105; 514/224.2, 230.5, 376; 548/219
See application file for complete search history.

(56) References Cited

OTHER PUBLICATIONS

Bartroli J et al., "New azole antifungals 3. Synthesis and antifungal activity el 3-substituted 4-(3H)-quinazolinones". Journal of Medicinal Chemistry, American Chemical Society, vol. 41, No. 11 Jan. 1, 1998, pp. 1869-1882.
Bravo H.R. et al., "Antimicrobial Activity of natural 2-Benzoxazolinones and Related Derivatives". Journal of Agricultural and Food Chemistry, vol. 45, 1997, pp. 3255-3257.
Budavari et al., "Merck Index". 1996 Merck Research Laboratories. p. 1002.
Patani G A et al., "Bioisosterism: A Rational Approach in Drug Design". Chemical Reviews, ACS. vol. 96, No. 8, Jan. 1, 1996, pp. 3147-3176.
Kitazaki T et al., "Optically Active Antifungal Azole, VIII. Synthesis and Antifungal Activity of 1-[(1R, 2R)-2-(2,4-Diflouro- and 2-Flourophenyl)-2-hydroxy-1-methyl-3(1H-1,2,4-triazol-1-yl)propyl]-3-(4-substituted phenyl-2(1H,3H)-imidazolenes and 2-Imidazolidinones". Chemical and Pharmaceutical Bulletin. vol. 47, No. 3, 1999, pp. 3451-359.
Fringuelli R et al., "Azole derivatives of 1,4-benzothiazine as antifungal agents". Bioorganic & Medicinal Chemistry. vol. 6, 1998 pp. 103-108.
Corrales et al., "Comparative Efficacies of TAK-187, a Long-Lasting Ergosterol Biosynthesis Inhibitor, and Benznidazole in Preventing Cardiac Damage in a Murine Model of Chagas' Disease." Antimicrobial Agents and Chemotherapy. Apr. 2005 p. 1556-1560.
Lebouvier et al., "Synthesis and antifungal activities of new fluconazole analogues with azaheterocycle moeity." Bioorganic & Medicinal Chemistry Letters 17 (2007) 3686-3689.
Zhao et al., "Design, synthesis, and Antifungal Activities of Novel 1H-Triazole Derivatives Based on the Structure of the Active Site of Fungal Lanosterol 14a-Demethylase (CYP51)." Chemistry and Biodiversity vol. 4 (2007) 1472-1479.
Tasaka et al., Optically Active Antifungal Azoles I. Synthesis and Antifungal Activity of )(2R,3R)-2-(2,4-Difluorophenyl)-3-mercapto-1-(1H-1,2,4-triazol-1-yl)-2-butanol and Its Stereoisomers.: Chem. Pharm. Bull. 41(6) 1035-1042 (1993).
Meerpoel et al., "Synthesis and in Vitro and in Vivo Structure-Activity Relationships of Novel Antifungal Triazoles for Dermatology." J. Med. Chem. 2005, 48, 2184-2193.
Bartroli et al., "Aldol Condensation of Evans Chiral Enolates with Acetophenones. its Appliation to the Stereoselective Synthesis of Homochiral Antifungal Agents." J. Org. Chem. 1995, 60, 3000-3012.
Heravi et al., "Synthesis of Some New Propanol Derivaties Analogous to Fluconazole." Phosphorus, Sulfur, and Silicon and the Related Elements, (2004) 179:11, 2329-2334.
Bartroli et al., "New Azole Antifungals. 2. Synthesis and Antifungal Activity of Heterocyclecarboxamide Derivatives of 3-Amiono-2-aryl-1-azolyl-2-butanol." J. Med. Chem. 1998, 41, 1855-1868.

Primary Examiner — Kahsay T Habte
(74) Attorney, Agent, or Firm — Kramer & Amado, PC

(57) ABSTRACT

The present invention discloses novel compounds of the Formula (1), comprising benzothiazinone, benzoxazinone or benzoxazolinone moieties having antifungal activity, method for preparing these compounds and the use of these compounds as antifungal agents in prevention and treatment of fungal infections, and pharmaceutical preparations containing these novel compounds.

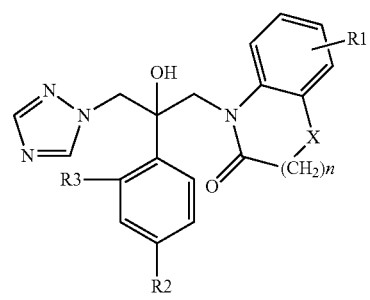

8 Claims, No Drawings

ANTIFUNGAL COMPOUNDS CONTAINING BENZOTHIAZINONE, BENZOXAZINONE OR BENZOXAZOLINONE AND PROCESS THEREOF

TECHNICAL FIELD

The present invention relates to novel compounds of the Formula 1 comprising benzothiazinone, benzoxazinone or benzoxazolinone moieties having antifungal activity and pharmaceutically acceptable salts thereof, methods for preparing these compounds and the use of these compounds as antifungal agents.

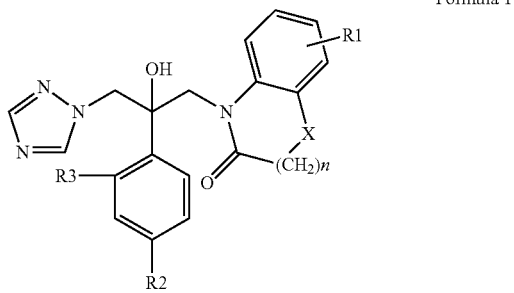

Formula 1 wherein, X is oxygen or sulphur; R1 is H, Cl, Br, F, Me, OMe, Ac or $NO_2$; R2 and R3 may be the same or different and each represents a hydrogen or halogen selected from fluorine, chlorine or bromine and n=0 or 1.

BACKGROUND AND PRIOR ART

The patients suffering from AIDS, organ transplant recipients and bone marrow transplant recipients have high risk of fungal infections. The total number of these types of patients is increasing in recent years and there is need to develop effective antifungal agents. There are various antifungal agents used to fight against fungal infections out of which fluconazole is an important azole antifungal. It is orally active and has low toxicity so it is widely used but its extensive use has resulted in emergence of fluconazole-resistant fungal strains. It is therefore necessary to develop novel antifungal agents effective against resistant strains. Worldwide efforts to obtain fluconazole analogues effective against resistant strains have resulted in synthesis of many novel azole antifungals. The structure-activity relationship studies have shown that presence of one triazole ring, halogenated phenyl ring and tertiary alcoholic oxygen functionality in fluconazole are necessary structural features essential for activity exhibited by fluconazole. The present invention seeks to provide novel azole antifungal compounds comprising benzothiazinone, benzoxazinone or benzoxazolinone moieties and process thereof as an effort to come up with antifungal agents with broad spectrum of antifungal activity. Fluconazole analogues have been reported to exhibit antifungal activity in the literature. Some of the references describing synthesis and antifungal activity of fluconazole analogues are:

Chem Pharm Bull 41, 1035 (1993); J Org Chem 60, 3000 (1995); J Med Chem 41 (11), 1855 (1998); J Med Chem 41 (11), 1869 (1998); Phosphorus Sulfur and Silicon 179, 2329-34 (2004); J Med Chem 48 (6), 2184-93 (2005); Antimicrobial Agents Chemotherapy 49 (4), 1556 (2005); Chemistry and Biodiversity 4, 1472-9 (2007); Bioorg Med Chem Lett 17 (13), 3686-9 (2007).

The compounds described in the present invention are novel compounds with enhanced antifungal activity and hence the protection is sought for the same.

OBJECTS OF THE INVENTION

The primary objective of the present invention is to provide compounds of Formula 1, containing benzothiazinone, benzoxazinone or benzoxazolinone moieties with enhanced antifungal activity against various fungi.

Another objective of the present invention is to provide the process for the preparation of the antifungal compounds of formula 1.

SUMMARY OF THE INVENTION

Accordingly, to meet the above stated objective, the present invention discloses novel fluconazole analogues of Formula 1 containing benzothiazinone, benzoxazinone or benzoxazolinone moieties, which are useful as antifungal compounds with enhanced activity.

In one aspect, the invention provides novel compounds of formula 1,

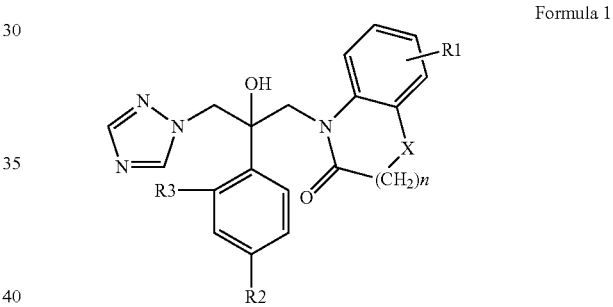

Formula 1 wherein, X is oxygen or sulphur; R1 is H, Cl, Br, F, Me, OMe, Ac or $NO_2$; R2 and R3 may be the same or different and each represents a hydrogen or halogen selected from fluorine, chlorine or bromine and n=0 or 1.

In another aspect, the invention provides a process for the preparation of the compounds of Formula 1 using various synthetic methods. Accordingly, the present invention describes a general process for the preparation of compounds of the Formula 1 wherein X, R1, R2, R3 and n are as defined above, which comprises reacting substituted benzothiazinone, benzoxazinone or benzoxazolinone moieties of the Formula 2 with epoxide of the Formula 3 in presence of a suitable base to obtain the compounds of the Formula 1.

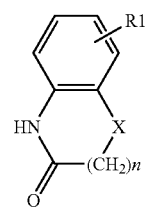

Formula 2

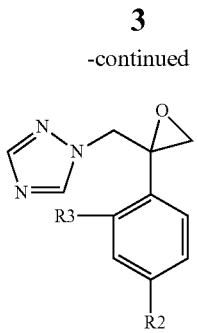

Formula 3

The said suitable base may be selected from various bases well described in the art. In yet another aspect, the invention discloses the use of compounds of formula 1 as antifungal agents.

DETAILED DESCRIPTION

The invention will now be described in detail in connection with certain preferred and optional embodiments, so that various aspects thereof may be more fully understood and appreciated.

According to the present invention, there are provided novel antifungal compounds of Formula 1. These compounds are analogues of fluconazole that are active against fungi and can be used in pharmaceutical preparations as active agents.

In a preferred embodiment, there are provided the novel compounds of Formula 1 wherein, X is oxygen or sulphur; R1 is H, Cl, Br, F, Me, OMe, Ac or $NO_2$; R2 and R3 may be the same or different and each represents a hydrogen or halogen selected from fluorine, chlorine or bromine and n=0 or 1.

In another preferred embodiment, the invention describes process for preparation of the compounds of formula 1. The compounds of the present invention may be prepared by adapting the route depicted in Scheme 1. The compounds of Formula 2 are reacted with the compounds of Formula 3 in presence of a suitable base to obtain the compounds of. Formula 1 wherein X is oxygen or sulphur; R1 is H, Cl, Br, F, Me, OMe, Ac or $NO_2$; R2 and R3 may be the same or different and each represents a hydrogen or halogen selected from fluorine, chlorine or bromine and n=0 or 1.

Scheme 1

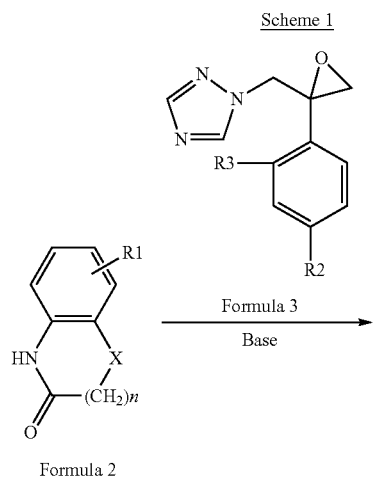

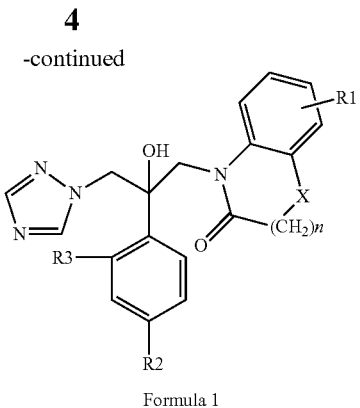

Formula 1

Accordingly, the general process for the preparation of compounds of Formula 1 comprises treating the compound of Formula 2 wherein X is oxygen or sulphur; R1 is H, Cl, Br, F, Me, OMe, Ac or $NO_2$ and n=0 or 1 with epoxide of Formula 3, wherein R2 and R3 may be the same or different and each represents a hydrogen or halogen selected from fluorine, chlorine or bromine, in presence of a base with or without addition of a phase transfer agent, to obtain the compound of Formula 1.

The said suitable base may be selected from potassium carbonate, sodium carbonate or cesium carbonate. The said phase transfer agent may be selected from tetrabutylammonium bromide, tetrabutylammonium chloride or tetrabutylammonium bisulfate.

In another embodiment, the invention discloses use of compounds of Formula 1 as antifungal agents.

In another preferred embodiment, the invention discloses pharmaceutical preparations which comprise a compound of Formula 1 in association with at least one pharmaceutical excipient known in art. These excipients are added to the composition for a variety of purposes.

The pharmaceutical preparations can be selected from various dosage forms such as solid dosage form like tablets, capsules, pellets, powders, soft gelatin capsules, and the like and oral liquids. The tablets can be prepared as conventional dosage forms such as immediate release, sustained release, modified release or controlled release.

The pharmaceutical compositions can be prepared using conventional techniques well known in the art.

According to another embodiment, the invention provides method for treating or preventing antifungal infections in a subject, wherein said method comprises administering therapeutically effective amounts of the compounds of formula 1 of the present invention or pharmaceutical composition comprising the same. The compounds of the present invention can also be administered optionally with other actives depending on the disease conditions.

As used herein the term "therapeutically effective amount" means an amount used in the pharmaceutical preparations to achieve the desired therapeutic effect.

The amount/quantity of the compound used in pharmaceutical compositions of the present invention will vary depending upon the body weight of the patient and the mode of administration and can be of any effective amount to achieve the desired therapeutic effect.

The invention further provides use of the compounds of Formula 1 in the preparation of pharmaceutical medicament.

The invention is further illustrated with the following examples and should not be construed to limit the scope of the present invention. The features of the present invention will become more apparent from the following description of the inventive concept and the description of the preferred embodiments and appended claims.

EXAMPLE 1

General Procedure for the Synthesis of Fluconazole Analogues of Formula 1

To a flame dried $K_2CO_3$ (0.18 mol), tetra-butylammonium bromide (TBAB, 0.09 mol) was added followed by the addition of compound of Formula 2 (0.09 mol) in dry ethyl acetate or dimethyl formamide (200 mL). Reaction mixture was stirred at 70-90° C. for 30 min. Then epoxide of Formula 3 (0.09 mol) dissolved in dry ethyl acetate or dimethyl formamide (200 mL) was added to the reaction mixture drop wise over a period of 10 min and stirring was continued for further 10-40 h at the same temperature. It was then cooled to room temperature, diluted with water (800 mL), extracted with ethyl acetate (3×400 mL), dried over $Na_2SO_4$, concentrated and purified by column chromatography to give pure compound.

Various compounds were prepared by using the general procedure described above and spectral data for some of the compounds are given below.

1) 4-[2-(2,4-Difluorophenyl)-2-hydroxy-3-[1,2,4] triazol-1-yl-propyl]-4H-benzo[1,4]thiazin-3-one (1a)

The compound of Formula 2a [compound of formula 2 wherein R1=H, X=S and n=1] (348 mg, 2.11 mmol) in dry ethyl acetate (10 mL) was added to a mixture of a flame dried $K_2CO_3$ (583 mg, 4.22 mmol) and tetra-butylammonium bromide (TBAB, 817 mg, 2.53 mmol) in dry ethyl acetate (40 mL). Reaction mixture was stirred at 80° C. for 30 min. Then epoxide of Formula 3a [compound of Formula 3 wherein R2=R3=F] (500 mg, 2.11 mmol) dissolved in dry ethyl acetate (20 mL) was added to the refluxing mixture drop wise over a period of 10 min and stirring was continued for further 15 h at the same temperature. It was then cooled to room temperature, diluted with water (100 mL), extracted with ethyl acetate (3×40 mL), dried over $Na_2SO_4$, concentrated and purified by column chromatography to give pure compound (662 mg); Yield: 78%; $^1H$ NMR (400 MHz, $CDCl_3$): δ 3.17 (d, J=14 Hz, 1H), 3.24 (d, J=14 Hz, 1H), 4.43 (d, J=14 Hz, 1H), 4.48 (d, J=14 Hz, 1H), 4.60 (s, 2H), 5.52 (bs, 1H), 6.41-6.47 (m, 1H), 6.68-6.73 (m, 1H), 6.92-6.98 (m, 1H), 7.13-7.26 (m, 3H), 7.50-7.58 (m, 1H), 7.76 (s, 1H), 8.15 (s, 1H).

2) 7-Chloro-4-[2-(2,4-difluorophenyl)-2-hydroxy-3-[1,2,4]-triazol-1-yl-propyl]-4H-benzo[1,4]thiazin-3-one (1b)

A mixture of compound of Formula 2b [compound of formula 2 wherein R1=7-Cl, X=S and n=1] (600 mg, 3 mmol), flame dried $K_2CO_3$ (622 mg, 4.5 mmol) and epoxide of Formula 3a [compound of Formula 3 wherein R2=R3=F] (711 mg, 3 mmol) was taken in 250 ml round bottom flask and dry dimethyl formamide (40 mL) was added. Reaction mixture was stirred at 85° C. for 25 h. It was then cooled to room temperature, diluted with water (200 mL), extracted with ethyl acetate (3×100 mL), dried over $Na_2SO_4$, concentrated and purified by column chromatography to give pure compound (957 mg); Yield: 73%; $^1H$ NMR (200 MHz, $CDCl_3$): δ 3.14 (d, J=14 Hz, 1H), 3.26 (d, J=14 Hz, 1H), 4.29 (d, J=14 Hz, 1H), 4.49 (d, J=14 Hz, 1H), 4.56 (d, J=14 Hz, 1H), 4.66 (d, J=14 Hz, 1H), 5.71 (bs, 1H), 6.42-6.56 (m, 1H), 6.63-6.78 (m, 1H), 7.06-7.21 (m, 3H), 7.40-7.52 (m, 1H), 7.80 (s, 1H), 8.25 (s, 1H).

3) 4-[2-(2,4-Difluorophenyl)-2-hydroxy-3-[1,2,4]-triazol-1-yl-propyl]-4H-benzo[1,4]oxazin-3-one (1i)

To a flame dried $K_2CO_3$ (232 mg, 1.69 mmol), tetra-butylammonium bromide (327 mg, 1.01 mmol) was added followed by the addition of compound of Formula 2i [Compound of Formula 2 wherein R1=H, X=O and n=1] (115 mg, 0.85 mmol) in dry ethyl acetate (10 mL). Reaction mixture was stirred at reflux for 30 min. Then epoxide of Formula 3a [compound of Formula 3 wherein R2=R3=F] (200 mg, 0.85 mmol) dissolved in dry ethyl acetate (10 mL) was added to the refluxing mixture drop wise over a period of 10 min and stirring was continued for further 16 h at the same temperature. It was then cooled to room temperature, diluted with water (50 mL), extracted with ethyl acetate (3×30 mL), dried over $Na_2SO_4$, concentrated and purified by column chromatography to give pure compound (251 mg); Yield: 79%; $^1H$ NMR (200 MHz, $CDCl_3+DMSO-d_6$): δ 4.14 (d, J=14 Hz, 1H), 4.49-4.70 (m, 4H), 4.94 (d, J=14 Hz, 1H), 5.98 (s, 1H), 6.70-6.80 (m, 2H), 6.82-7.00 (m, 3H), 7.10-7.22 (m, 1H), 7.35-7.49 (m, 1H), 7.62 (s, 1H), 8.22 (s, 1H).

4) 7-Bromo-4-[2-(2,4-difluorophenyl)-2-hydroxy-3-[1,2,4]triazol-1-yl-propyl]-4H-benzo[1,4]thiazin-3-one (1c)

Yield: 72%; $^1H$ NMR (200 MHz, $CDCl_3$): δ 3.22 (d, J=14 Hz, 1H), 3.36 (d, J=14 Hz, 1H), 4.28 (d, J=14 Hz, 1H), 4.67 (d, J=14 Hz, 1H), 4.73 (d, J=14 Hz, 1H), 4.85 (d, J=14 Hz, 1H), 5.72 (bs, 1H), 6.56-6.67 (m, 1H), 6.70-6.85 (m, 1H), 7.18 (d, J=8 Hz, 1H), 7.34 (dd, J=8, 2 Hz, 1H), 7.41 (d, J=2 Hz, 1H), 7.43-7.55 (m, 1H), 7.97 (bs, 1H), 8.90 (bs, 1H).

5) 4-[2-(2,4-Difluorophenyl)-2-hydroxy-3-[1,2,4] triazol-1-yl-propyl]-7-methoxy-4H-benzo[1,4]thiazin-3-one (1d)

Yield: 77%; $^1H$ NMR (200 MHz, $CDCl_3$): δ 3.15 (d, J=10 Hz, 1H), 3.22 (d, J=10 Hz, 1H), 3.70 (s, 3H), 4.38 (s, 2H), 4.54 (s, 2H), 5.89 (bs, 1H), 6.35-6.49 (m, 1H), 6.61-6.76 (m, 3H), 7.10 (d, J=10 Hz, 1H), 7.42-7.58 (m, 1H), 7.76 (s, 1H), 8.13 (s, 1H).

6) 4-[2-(2,4-Difluorophenyl)-2-hydroxy-3-[1,2,4] triazol-1-yl-propyl]-7-methyl-4H-benzo[1,4]thiazin-3-one (1e)

Yield: 79%; $^1H$ NMR (200 MHz, $CDCl_3$): δ 2.28 (s, 3H), 3.20 (d, J=12 Hz, 1H), 3.28 (d, J=12 Hz, 1H), 4.48 (s, 2H), 4.61 (s, 2H), 5.92 (bs, 1H), 6.42-6.56 (m, 1H), 6.68-6.88 (m, 2H), 6.99-7.16 (m, 2H), 7.49-7.64 (m, 1H), 7.82 (s, 1H), 8.20 (s, 1H).

7) 7-Chloro-4-[2-(4-fluorophenyl)-2-hydroxy-3-[1,2,4]-triazol-1-yl-propyl]-4H-benzo[1,4]thiazin-3-one (1f)

Yield: 74%; $^1H$ NMR (200 MHz, $CDCl_3$): δ 3.27 (d, J=14 Hz, 1H), 3.40 (d, J=14 Hz, 1H), 4.11 (d, J=14 Hz, 1H), 4.66 (d, J=14 Hz, 1H), 4.69-4.83 (m, 2H), 6.87-6.95 (m, 2H), 7.15 (dd, J=8, 2 Hz, 1H), 7.30-7.40 (m, 4H), 7.94 (s, 1H), 8.67 (s, 1H).

8) 4-[2-(4-Bromophenyl)-2-hydroxy-3-[1,2,4]triazol-1-yl-propyl]-7-methoxy-4H-benzo[1,4]thiazin-3-one (1g)

Yield: 77%; $^1$H NMR (200 MHz, CDCl$_3$): δ 3.26 (d, J=14 Hz, 1H), 3.37 (d, J=14 Hz, 1H), 3.78 (s, 3H), 4.22 (d, J=14 Hz, 1H), 4.52 (d, J=14 Hz, 1H), 4.60-4.75 (m, 2H), 6.72 (dd, J=10, 4 Hz, 1H), 6.80 (d, J=4 Hz, 1H), 7.17-7.31 (m, 5H), 7.94 (s, 1H), 8.53 (s, 1H).

9) 4-[2-(4-Fluorophenyl)-2-hydroxy-3-[1,2,4]triazol-1-yl-propyl]-7-methoxy-4H-benzo[1,4]thiazin-3-one (1h)

Yield: 78%; $^1$H NMR (200 MHz, CDCl$_3$): δ 3.26 (d, J=14 Hz, 1H), 3.37 (d, J=14 Hz, 1H), 3.78 (s, 3H), 4.22 (d, J=14 Hz, 1H), 4.54 (d, J=14 Hz, 1H), 4.61 (d, J=14 Hz, 1H), 4.70 (d, J=14 Hz, 1H), 6.71-6.91 (m, 4H), 7.23-7.33 (m, 3H), 7.91 (s, 1H), 8.41 (s, 1H).

10) 6-Chloro-4-[2-(2,4-difluorophenyl)-2-hydroxy-3-[1,2,4]triazol-1-yl-propyl]-4H-benzo[1,4]oxazin-3-one (1j)

Yield: 74%; $^1$H NMR (200 MHz, CDCl$_3$): δ 4.13 (d, J=15 Hz, 1H), 4.35-4.62 (m, 4H), 5.03 (d, J=15 Hz, 1H), 5.53 (bs, 1H), 6.66-6.98 (m, 4H), 7.23 (d, J=2 Hz, 1H), 7.49-7.64 (m, 1H), 7.82 (bs, 1H), 8.09 (bs, 1H).

11) 6-Bromo-4-[2-(2,4-difluorophenyl)-2-hydroxy-3-[1,2,4]triazol-1-yl-propyl]-4H-benzo[1,4]oxazin-3-one (1k)

Yield: 73%; $^1$H NMR (200 MHz, CDCl$_3$): δ 4.11 (d, J=14 Hz, 1H), 4.49-4.74 (m, 4H), 5.06 (d, J=14 Hz, 1H), 5.55 (bs, 1H), 6.68-6.85 (m, 3H), 7.08 (dd, J=10, 2 Hz, 1H), 7.32 (d, J=2 Hz, 1H), 7.46-7.60 (m, 1H), 7.87 (s, 1H), 8.51 (s, 1H).

12) 4-[2-(2,4-Difluorophenyl)-2-hydroxy-3-[1,2,4]triazol-1-yl-propyl]-6-nitro-4H-benzo[1,4]oxazin-3-one (1l)

Yield: 67%; $^1$H NMR (200 MHz, CDCl$_3$): δ 4.16 (d, J=14 Hz, 1H), 4.54 (d, J=14 Hz, 1H), 4.61-4.82 (m, 3H), 5.12 (d, J=16 Hz, 1H), 5.57 (bs, 1H), 6.68-6.86 (m, 2H), 7.05 (d, J=10 Hz, 1H), 7.52-7.66 (m, 1H), 7.82 (s, 1H), 7.93 (dd, J=10, 2 Hz, 1H), 8.02 (s, 1H), 8.28 (d, J=2 Hz, 1H).

13) 6-Acetyl-4-[2-(2,4-difluorophenyl)-2-hydroxy-3-[1,2,4]-triazol-1-yl-propyl]-4H-benzo[1,4]oxazin-3-one (1m)

Yield: 81%; $^1$H NMR (200 MHz, CDCl$_3$): δ 2.59 (s, 3H), 4.30 (d, J=14 Hz, 1H), 4.60-4.79 (m, 4H), 5.09 (d, J=14 Hz, 1H), 6.68-6.84 (m, 2H), 7.03 (d, J=8 Hz, 1H), 7.51-7.67 (m, 2H), 7.87 (bs, 1H), 7.91 (d, J=2 Hz, 1H), 8.31 (bs, 1H).

14) 4-[2-(4-Bromophenyl)-2-hydroxy-3-[1,2,4]-triazol-1-yl-propyl]-6-chloro-4H-benzo[1,4]oxazin-3-one (1n)

Yield: 74%; $^1$H NMR (200 MHz, CDCl$_3$): δ 3.93 (d, J=14 Hz, 1H), 4.53-4.69 (m, 4H), 4.85 (d, J=14 Hz, 1H), 6.86-6.99 (m, 2H), 7.30-7.45 (m, 4H), 7.88 (s, 1H), 8.35 (s, 1H).

15) 6-Chloro-4-[2-(4-fluorophenyl)-2-hydroxy-3-[1,2,4]triazol-1-yl-propyl]-6-chloro-4H-benzo[1,4]oxazin-3-one (1o)

Yield: 73%; $^1$H NMR (200 MHz, CDCl$_3$): δ 3.95 (d, J=14 Hz, 1H), 4.52-4.68 (m, 4H), 4.85 (d, J=14 Hz, 1H), 6.86-7.03 (m, 4H), 7.34 (d, J=2 Hz, 1H), 7.41-7.47 (m, 2H), 7.87 (s, 1H), 8.28 (s, 1H).

16) 6-Acetyl-4-[2-(4-bromophenyl)-2-hydroxy-3-[1,2,4]triazol-1-yl-propyl]-4H-benzo[1,4]oxazin-3-one (1p)

Yield: 80%; $^1$H NMR (200 MHz, CDCl$_3$): δ 2.49 (s, 3H), 4.06 (d, J=14 Hz, 1H), 4.50-4.64 (m, 4H), 4.79 (d, J=8 Hz, 1H), 6.92 (d, J=8 Hz, 1H), 7.27-7.35 (m, 4H), 7.53 (dd, J=8, 2 Hz, 1H), 7.84-7.86 (m, 2H), 8.38 (s, 1H).

17) 3-[2-(2,4-Difluorophenyl)-2-hydroxy-3-[1,2,4]triazol-1-yl-propyl]-3H-benzoxazolin-2-one (1q)

Yield: 81%; $^1$H NMR (200 MHz, CDCl$_3$+DMSO-d$_6$): δ 4.35 (d, J=14 Hz, 1H), 4.43 (d, J=14 Hz, 1H), 4.90 (d, J=14 Hz, 1H), 5.03 (d, J=14 Hz, 1H), 6.36 (bs, 1H), 6.89-7.02 (m, 1H), 7.05-7.38 (m, 5H), 7.43-7.57 (m, 1H), 7.80 (s, 1H), 8.43 (s, 1H).

EXAMPLE 2

Preparation of 1-[2-(2,4-difluorophenyl)-oxiranylmethyl]-1H-[1,2,4]triazole of Formula 3 wherein R2=R3=F A mixture of 1-(2,4-difluorophenyl)-2-(1H-1,2,4-triazolyl)-ethanone (0.067 mol, 15.00 g), trimethylsulfoxonium iodide (0.1 mol, 22.20 g), and cetrimide (0.00067 mol, 0.245 g) in dichloromethane (150 mL) was stirred at room temperature for 10 min. Then a solution of KOH (0.168 mol, 9.42 g) in water (20 mL) was added to it. This mixture was refluxed at 40-45° C. for 12 h, cooled to room temperature and diluted with water (60 mL). The two layers were separated, the aqueous layer was extracted with dichloromethane (3×150 mL) and the combined organic extracts were dried over Na$_2$SO$_4$. After the solvent was concentrated in vacuo, the residue was subjected to chromatography on silica gel to afford pure epoxide of Formula 3 wherein R2=R3=F (13.55 g, 85%); $^1$H NMR (200 MHz, CDCl$_3$+CCl$_4$): δ 2.85 (d, J=6 Hz, 1H), 2.95 (d, J=6 Hz, 1H), 4.50 (d, J=16 Hz, 1H), 4.80 (d, J=16 Hz, 1H), 6.76-6.89 (m, 2H), 7.12-7.26 (m, 1H), 7.83 (s, 1H), 8.07 (s, 1H).

The other epoxides were prepared from corresponding ethanones using same procedure.

1-[2-(2,4-Dichlorophenyl)-oxiranylmethyl]-1H-[1,2,4]triazole of Formula 3 wherein R2=R3=Cl Yield: 91%; $^1$H NMR (200 MHz, CDCl$_3$+CCl$_4$): δ 2.92 (d, J=4 Hz, 1H), 3.01 (d, J=4 Hz, 1H), 4.53 (d, J=14 Hz, 1H), 4.90 (d, J=14 Hz, 1H), 7.16-7.46 (m, 3H), 7.92 (s, 1H), 8.13 (s, 1H).

1-[2-(4-Bromophenyl)-oxiranylmethyl]-1H-[1,2,4]triazole of Formula 3 wherein R2=Br, R3=H Yield: 84%; $^1$H NMR (200 MHz, CDCl$_3$+CCl$_4$): δ 2.81 (d, J=6 Hz, 1H), 2.87 (d, J=6 Hz, 1H), 4.59 (d, J=14 Hz, 1H), 4.80 (d, J=14 Hz, 1H), 7.20 (d, J=8 Hz, 2H), 7.47 (d, J=8 Hz, 2H), 7.89 (s, 1H), 8.08 (s, 1H).

EXAMPLE 3

Antifungal Activity Testing

The compounds of Formula 1 were tested for antifungal activity against various fungi including *Candida albicans, Aspergillus niger* and *Fusarium proliferatum*. In vitro evaluation of antifungal activity was performed by determining the minimum inhibitory concentration (MIC) following standard methods (CLSI: Reference method for broth dilution antifungal susceptibility testing of yeasts; Approved standard, second edition M27-A2, 2002; CLSI: Reference method for broth dilution antifungal susceptibility testing of filamentous fungi; Approved standard M38-A, 2002). Anti-fungal susceptibility testing of these anti-fungal compounds was done by broth dilution method using RPMI 1640 medium with MOPS buffer. Known anti-fungal agents like Fluconazole and Amphotericin-B were used as standards. End points were determined after 48 hours visually and by using spectrophotometer wherever necessary. The activity parameters are enumerated in Table 1 which shows that some of the compounds exhibited significant antifungal activity.

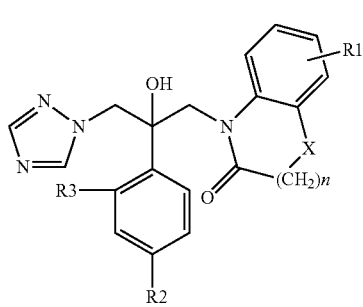

Formula 1

TABLE 1

| | | | MIC obtained by broth macro-dilution method | | |
|---|---|---|---|---|---|
| | | | Activity against organisms MIC in µg/ml | | |
| Sr no | Compound no | Structure 1 | C. albicans ATCC 24433 | A. niger ATCC 16404 | F. proliferatum ATCC 10052 |
| 1 | Fluconazole | | 1 | 128 | >128 |
| 2 | Amphotericin B | | 0.25 | 1 | 2 |
| 3 | 1a | n = 1, X = S, R1 = H, R2 = R3 = F | 0.25 | >64 | >64 |
| 4 | 1b | n = 1, X = S, R1 = 7-Cl, R2 = R3 = F | 1 | >16 | >16 |
| 5 | 1c | n = 1, X = S, R1 = 7-Br, R2 = R3 = F | 1 | >16 | >16 |
| 6 | 1d | n = 1, X = S, R1 = 7-OMe, R2 = R3 = F | 4 | >32 | >32 |
| 7 | 1e | n = 1, X = S, R1 = 7-Me, R2 = R3 = F | 2 | >32 | >32 |
| 8 | 1f | n = 1, X = S, R1 = 7-Cl, R2 = F, R3 = H | 2 | >16 | >16 |
| 9 | 1g | n = 1, X = S, R1 = 7-OMe, R2 = Br, R3 = H | 2 | >16 | >16 |
| 10 | 1h | n = 1, X = S, R1 = 7-OMe, R2 = F, R3 = H | 8 | >16 | >16 |
| 11 | 1i | n = 1, X = O, R1 = H, R2 = R3 = F | 0.5 | >64 | >64 |
| 12 | 1j | n = 1, X = O, R1 = 6-Cl, R2 = R3 = F | 8 | >32 | >32 |
| 13 | 1k | n = 1, X = O, R1 = 6-Br, R2 = R3 = F | 16 | >32 | >32 |
| 14 | 1l | n = 1, X = O, R1 = 6-NO$_2$, R2 = R3 = F | 32 | >32 | >32 |
| 15 | 1m | n = 1, X = O, R1 = 6-Ac, R2 = R3 = F | >64 | >64 | >64 |
| 16 | 1n | n = 1, X = O, R1 = 6-Cl, R2 = Br, R3 = H | 4 | >16 | >16 |
| 17 | 1o | n = 1, X = O, R1 = 6-Cl, R2 = F, R3 = H | 16 | >16 | >16 |
| 18 | 1p | n = 1, X = O, R1 = 6-Ac, R2 = Br, R3 = H | 32 | >32 | >32 |
| 19 | 1q | n = 0, X = O, R1 = H, R2 = R3 = F | 2 | >128 | >128 |

For Fluconazole and the novel compounds of formula 1, MIC is recorded as the concentration exhibiting 80% inhibition as compared to the positive growth control.

For Amphotericin B, MIC is recorded as the concentration exhibiting complete inhibition.

>16 μg/ml: The novel compounds of formula 1 are generally tested for concentration range from 0.03 μg/ml to the concentration till it was in solution (For e.g.: Back precipitation 128-32 μg/ml, Concentration for assay: 0.03 to 16 μg/ml).

The antifungal activity exhibited by the compounds in the present invention was confirmed by secondary screening against various strains and the results are shown in Table 2.

TABLE 2

MIC obtained by broth micro-dilution method

| Organisms | MIC in μg/ml | | | |
|---|---|---|---|---|
| | Amphotericin B | Fluconazole | 1a | 1i |
| C. albicans ATCC24433 | 0.25 | 0.25 | 0.03 | 0.12 |
| C. albicans ATCC10231 | 0.5 | 1.0 | 0.12 | 0.5 |
| C. albicans ATCC2091 | 0.5 | 4 | 2 | 4 |
| C. albicans ATCC90028 | 0.5 | 0.5 | 0.03 | 0.12 |
| C. glabrata ATCC90030 | 0.25 | 4 | 0.06 | 0.25 |
| C. krusei ATCC6258 | 0.5 | 64 | 4 | 16 |
| C. tropicalis ATCC750 | 0.5 | 2 | 0.5 | 2 |

For Fluconazole and the novel compounds of formula 1, MIC is recorded as the concentration exhibiting 50% inhibition as compared to the positive control.

For Amphotericin B, MIC is recorded as the concentration exhibiting complete inhibition It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The invention claimed is:

1. Antifungal compounds of Formula 1

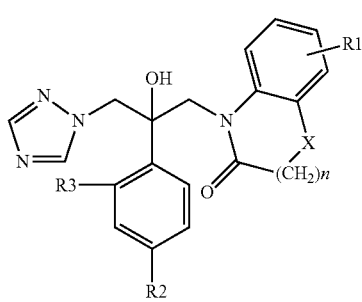

Formula 1 wherein X is oxygen or sulphur; R1 is H, Cl, Br, F, Me, OMe, Ac or NO$_2$; R2 and R3 may be the same or different and each represents a hydrogen or a halogen selected from fluorine, chlorine or bromine; and n=0 or 1.

2. A pharmaceutical composition comprising an antifungal compound of Formula 1 according to claim 1, in combination with at least one pharmaceutical excipient.

3. A method for treating a fungal infection in a subject, which method comprises administering to the said subject an effective amount of an antifungal compound of Formula 1 according to claim 1.

4. The method of claim 3, wherein said compound of Formula 1 is administered in combination with at least one pharmaceutical excipient.

5. A process of preparing an antifungal compound, comprising reacting a compound of Formula 2 with an epoxide of Formula 3 in the presence of a base, as set forth in Scheme 1, to obtain an antifungal compound of Formula 1, as set forth in Scheme 1:

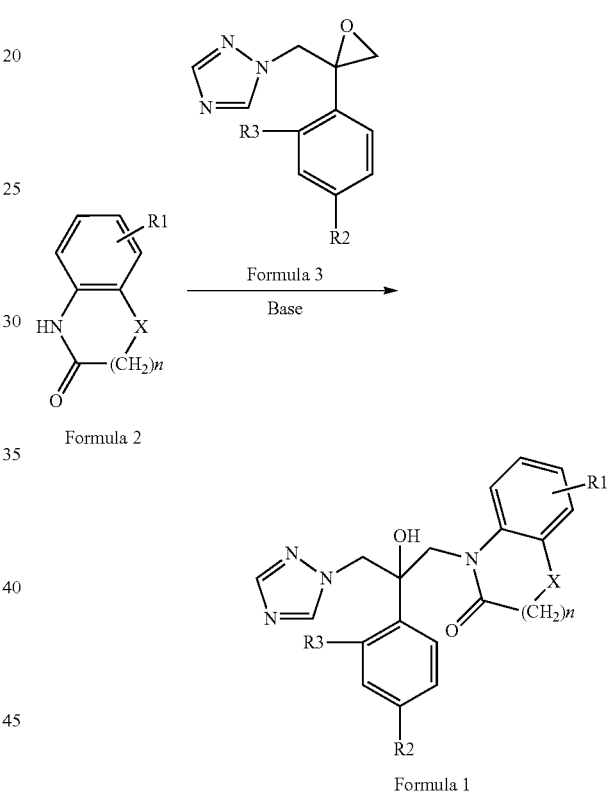

Scheme 1

Formula 2

Formula 3
Base

Formula 1 wherein X is oxygen or sulphur;
R1 is H, Cl, Br, F, Me, OMe, Ac or NO$_2$;
R2 and R3 may be the same or different and each represent a hydrogen or a halogen selected from fluorine, chlorine or bromine; and
n=0 or 1.

6. The method of claim 5, wherein the base is selected from a group consisting of potassium carbonate, sodium carbonate and cesium carbonate.

7. The method of claim 5, wherein said reacting in carried out in the presence of a base and a phase transfer agent.

8. The method of claim 7, wherein the phase transfer agent is selected from a group consisting of tetrabutylammonium bromide, tetrabutylammonium chloride and tetrabutylammonium bisulfate.

* * * * *